United States Patent

Honna et al.

[11] 4,224,450
[45] Sep. 23, 1980

[54] PROCESS FOR THE PREPARATION OF GLYOXAL-2-OXIMES

[75] Inventors: Takaji Honna; Motoaki Tanaka; Syozo Yamada; Hidekazu Miyake, all of Tokushima, Japan

[73] Assignee: Taiho Pharmaceutical Company, Tokyo, Japan

[21] Appl. No.: 67,888

[22] Filed: Aug. 20, 1979

Related U.S. Application Data

[62] Division of Ser. No. 16,821, Mar. 2, 1979.

[30] Foreign Application Priority Data

Mar. 9, 1978 [JP] Japan ................................. 53-27300

[51] Int. Cl.² .................... C07D 261/14; A61K 31/42
[52] U.S. Cl. ..................................... 548/248; 424/272
[58] Field of Search ......................................... 548/248

Primary Examiner—Anton H. Sutto
Attorney, Agent, or Firm—Murray and Whisenhunt

[57] ABSTRACT

Novel derivatives of glyoxal-2-oxim represented by the chemical formula

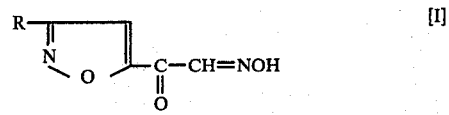

wherein R is hydrogen or a lower alkyl or phenyl group, are provided in accordance with the present invention. These derivatives are prepared by reacting the corresponding isoxazole-5-carbaldehyde with nitromethane in the presence of a metal alkoxide, or the corresponding 5-acetylisoxazole with a nitrite. They have anti-inflammatory and/or analgesic activities.

2 Claims, No Drawings

PROCESS FOR THE PREPARATION OF GLYOXAL-2-OXIMES

This is a division, of application Ser. No. 016,821 filed Mar. 2, 1979.

This invention relates to novel glyoxal-2-oxim derivatives and a process for the preparation thereof. The glyoxal-2-oxim derivatives of the present invention are compounds represented by the formula,

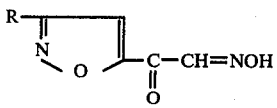  [I]

wherein R is hydrogen or a lower alkyl or phenyl group. The lower alkyl group represented by R in the above formula includes methyl, ethyl, propyl and butyl groups. The above compounds of the present invention are all novel and exhibit pharmacological activities such as anti-inflammatory and/or analgesic activities which appear useful as medicines.

The compounds represented by formula [I] may be prepared, for example, by reacting a compound of the formula,

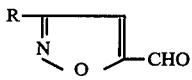  [II]

wherein R is defined as above, with nitromethane in the presence of an excess of a basic compound.

The following description is made for detailed explanation of the present invention. Above compounds [II] are usually known or may be easily prepared by any known process [See "Gazz. Chim. Ital.", 73, 99, (1943); "Tetrahedron", 23, 4697, (1967)]. The reaction of compound [II] with nitromethane is usually and advantageously carried out in a solvent in the presence of a basic compound. As the basic compound metal alkoxides may be generally employed. The metal of said metal alkoxides includes metals such as sodium, potassium, aluminium and magnesium, and said alkoxides are lower alkoxides including methoxide, ethoxide, propoxide and butoxide. An appropriate solvent may be used in the reaction unless it affects the reaction, but lower alcohols such as methanol, ethanol, propanol and butanol may preferably be used. An appropriate ratio of nitromethane to compound [II] may be selected and it is generally advantageous to use a ratio of 1-2 to 1 on the gram-equivalent basis. Also the ratio of a metal alkoxide to compound [II] used should generally be such that an amount of the metal alkoxide is in excess of compound [II], and the alkoxide is preferably used in an amount as large as 1.1-2.0 equivalents per equivalent of compound [II].

The reaction temperature in the above reaction may freely be decided but generally the reaction advantageously proceeds within the temperature range of from −20° to 60° C. The resulting metal salt, after or without isolation, is then acidified with a mineral acid such as hydrochloric acid, sulfuric acid, or the like to produce compound [I] of the present invention, which can be easily isolated by a conventional separating means.

Compound [I] of the present invention may also be prepared by reacting a compound represented by the formula,

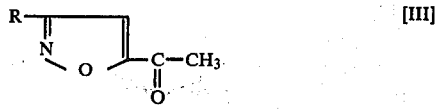  [III]

wherein R is the same as defined above, with a compound of the formula, R'ONO [IV] wherein R' represents hydrogen or a lower alkyl group. Compounds [III] are usually publicly known ones or those readily prepared by any publicly known process. [See, Gazz. Chim. Ital., 70, 676, (1940); Ibid., 72, 155, (1942); Ibid., 73, 99, (1943)]. Also, compounds [IV] are usually known ones, and the lower alkyl group represented by R' includes, for example, methyl, ethyl, propyl, butyl and amyl groups. The reaction between compounds [III] and [IV] is usually carried out in a solvent in the presence or absence of a catalyst. The catalyst which may be employed includes acidic compounds such as gaseous hydrogen chloride, hydrochloric acid, sulfuric acid and acetic acid, and basic compounds which are metal alkoxides such as sodium methoxide, sodium ethoxide, pottasium methoxide and pottasium ethoxide. The solvents used in the present reaction are not particularly limited so far as they do not affect the reaction, but ethers, lower alcohols, acetic acid and the like may be preferred. An appropriate ratio of compounds [IV] to [III] may be selected but generally it is advantageous to use 1–3 equivalents of compound [IV] per equivalent of compound [III]. An appropriate temperature may also be selected, but the reaction proceeds favorably within the temperature range of −10° C. to 50° C. Compounds [I] of the present invention having been produced by the above reaction can be isolated by a conventional means.

The particularly preferred compounds of the present invention includes (3-methylisoxazole-5-yl)-glyoxal-2-oxim and (3-phenylisoxazole-5-yl)glyoxal-2-oxim. Additionally, (3-ethylisoxazole-5-yl)glyoxal-2-oxim, (3-isopropylisoxazole-5-yl)glyoxal-2-oxim and (3-butylisoxazole-5-yl)glyoxal-2-oxim are also preferable.

In respect to the above two preferred compounds, biological activity tests have been conducted and the results are shown as below:

| Compound | Kind of Test | Acute toxicity ($LD_{50}$) | Anti-inflammatory activity (Carrageenin edema method) | Analgesic activity (Stretching method) |
|---|---|---|---|---|
| (3-Methylisoxazole-5-yl) glyoxal-2-oxim | | 890 mg/kg | 83% | 50% |
| (3-Phenylisoxazole-5-yl) glyoxal-2-oxim | | 1690 mg/kg | 56% | 75% |

TEST METHODS (1) Acute toxity

The compounds to be tested were suspended in 0.5% carboxymethyl cellulose solution, and the suspension was orally administrated in variable amounts in response to the weights of dd-strain male mice having those ranging from 20 to 25 g which were forced to abstain from food overnight. They were observed for seven days after said administration to seek $LD_{50}$ values by counting the number of dead mice.

(2) Anti-inflammatory activity (Carrageenin edema method)

The compounds to be tested were suspended in 0.5% carboxymethyl cellulose solution, and the suspension was orally administrated in 100 mg per kg of Wistar-strain male rats having their weight range of 130 to 170 g which were forced to abstain from food overnight. These rats were then injected subcutaneously into their left hind paws each with 0.1 ml of a physiological NaCl solution having dissolved therein carrageen in 1% concentration. After three hours from said injection, the rats were killed, both hind legs were cut out and promptly weighed. There is assumed as weight of edema a value obtained by deducting a weight of untreated hind leg from that of the carrageenin injected hind leg of the rat. Inhibition ratio of a sample-administrated group to a control group has been sought. The control group was administrated only with 0.5% methyl cellulose solution in the same manner.

(3) Analgesic activity (Acetic acid stretching method)

After the compounds to be tested were orally administrated in 100 mg per kg of ddy-strain mice having their weight range of 20 to 25 g, 0.2 ml of 0.7% acetic acid was intra-peritoneally administrated to each animal to observe stretching sympton thereby having found the inhibition ratio (%).

The compounds of the present invention are suitable for the use of an anti-inflammatory agent and/or an analgesic agent. Clinical dosage of these compounds ranges usually from 50 to 1000 mg per day for adult, and preferably from 100 to 500 mg, which may be administrated two to three times a day. Dosage may be appropriately adjusted depending on individual cases such that patient's condition, age, etc. should be considered. Administration is conducted in many forms such as injections, oral administrative preparations, suppositories (rectal administrations) and external preparations.

The compounds of the present invention may be used as a pharmaceutical composition by being formulated with any and conventional pharmaceutically acceptable carrier or vehicle, in conventional manner.

Vehicles which may be used for preparation of oral administrative composition such as in tablet, capsule, granule and powder forms include those generally used in the art such as calcium carbonate, calcium phosphate, starch, sugar, lactose, talc, magnesium stearate, gellatin, polyvinyl pyrrolidone, gum arabic, sorbitol, microcrystalline cellulose, polyethylene glycol, carboxymethyl cellulose, Silica AEA ® (Sankyo Company Ltd.), TC-5 ® (Kyowa Hakko Kogyo Co., Ltd.), shellac, etc. Tablet may be coated by a method well known in the art. Liquid formulations for oral administration may be in the form of aqueous or oily suspension or solution, syrup, elixir and the like, and prepared by conventional means. Injectionable formulations may be aqueous or oily suspension or solution, powdery composition with a filler, and lyophilized preparation which are dissolved upon their use, or the lile. They may be prepared by conventional means.

The present compounds are also provided as a suppository composition for rectal administration, which may contain pharmaceutically acceptable carriers well known in the art such as polyethylene glycol, lanolin, cacao butter, Witepsol ® (Dynamite Nobel Co.) etc.

External preparation is applied preferably in the form of ointment or cream which may be prepared by conventional processes using ingredients which are usually employed.

The following examples, concretely illustrate the present invention.

EXAMPLE 1

In 50 ml of ethanol were dissolved 5.5 g of 3-methylisoxazole-5-carbaldehyde and 3.3 g of nitromethane. To the solution was added dropwise a solution of sodium ethoxide in ethanl, which had been prepared from 1.5 g of sodium and 30 ml of ethanol, while stirring at room temperature. After dropping the resultant was stirred for a further 3 hrs. at room temperature and then ether was added thereto to separate the sodium salt. This was dissolved in water, which was followed by acidification with hydrochloric acid. The resulting precipitate was filtered off and recrystallized from chloroform to obtain 5.4 g of (3-methylisoxazole-5-yl)glyoxal-2-oxim having m.p. of 179° C.–180° C. Yield, 70%.

| | Elemental Analysis ($C_6H_6N_2O_3$) | | |
|---|---|---|---|
| | C | H | N |
| Calcd. (%) | 46.76 | 3.92 | 18.18 |
| Found (%) | 46.59 | 3.92 | 17.90 |

EXAMPLE 2

In 40 ml of ethanol were dissolved 3.5 g of 3-phenylisoxazole-5-carbaldehyde and 1.3 g of nitromethane, and then cooled to 0°–5° C. While stirring the solution, a solution of sodium ethoxide in ethanol, which had been prepared from 0.6 g of sodium and 20 ml of ethanol, was dropwise added thereto. Stirring was continued for 24 hrs. at room temperature after completion of the dropwise addition, and the resultant solution was thereafter concentrated under reduced pressure. Ether was added thereto to separate the sodium salt, which was then dissolved in water. The aqueous solution was acidified with hydrochloric acid and then extracted with ether. The ether extract was dried over sodium sulfate and then ether was removed by distillation. The residue was recrystallized from chloroform to obtain 2.5 g of (3-phenylisoazole-5-yl) glyoxal-2-oxim having m.p. of 155° C.–157° C. Yield, 59%.

| Elemental Analysis ($C_{11}H_8N_2O_3$) | | | |
|---|---|---|---|
| | C | H | N |
| Calcd. (%) | 61.12 | 3.73 | 12.96 |
| Found (%) | 60.82 | 3.65 | 12.77 |

EXAMPLE 3

In 30 ml of ether was dissolved 2.5 g of 5-acetyl-3-methylisozazole. While gaseous hydrogen chloride was passed through the resultant solution with stirring, a solution of 4.5 g of amyl nitrite in 10 ml of ether was dropped thereinto. After a further one hour stirring at room temperature after completion of said dropwise addition, the resulting precipitate was isolated by filtration. Recrystallization from chloroform gave 1.0 g of (3-methylisoxazole-5-yl) glyoxal-2-oxim having m.p. of 179° C.–180° C. Yield, 27%.

| Elemental Analysis ($C_6H_6N_2O_3$) | | | |
|---|---|---|---|
| | C | H | N |
| Calcd. (%) | 46.76 | 3.92 | 18.18 |
| Found (%) | 46.57 | 4.01 | 18.02 |

What is claimed is:

1. A process for the preparation of a glyoxal-2-oxim derivative represented by the formula,

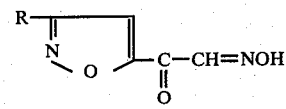

wherein R represents hydrogen, or a lower alkyl of $C_{1-4}$ or phenyl group, which comprises reacting a compound of

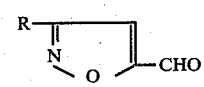

wherein R is defined as above, with nitromethane in the presence of an excess of a basic compound, at a temperature of $-20°$ C. to $60°$ C.

2. The process according to claim 1 wherein the basic compound is a metal alkoxide of $C_{1-4}$.